United States Patent
Uhlmann (10) Patent No.: US 9,630,841 B2
(45) Date of Patent: Apr. 25, 2017

(54) METHOD FOR PRODUCING AN AQUEOUS STABLE CHLORINE DIOXIDE SOLUTION

(75) Inventor: Helmut Uhlmann, Wuppertal (DE)

(73) Assignee: A.P.F. AQUA SYSTEM AG, Wuppertal (DE)

( * ) Notice: Subject to any disclaimer, the term of this patent is extended or adjusted under 35 U.S.C. 154(b) by 0 days.

(21) Appl. No.: 13/996,728

(22) PCT Filed: Dec. 22, 2011

(86) PCT No.: PCT/EP2011/006510
§ 371 (c)(1),
(2), (4) Date: Jun. 21, 2013

(87) PCT Pub. No.: WO2012/084247
PCT Pub. Date: Jun. 28, 2012

(65) Prior Publication Data
US 2013/0287722 A1 Oct. 31, 2013

(30) Foreign Application Priority Data
Dec. 23, 2010 (DE) .................. 10 2010 055 982

(51) Int. Cl.
| | | |
|---|---|---|
| *A61K 8/20* | (2006.01) | |
| *A61K 33/22* | (2006.01) | |
| *C01B 11/02* | (2006.01) | |
| *C02F 1/76* | (2006.01) | |
| *A01N 59/00* | (2006.01) | |
| *B01J 19/00* | (2006.01) | |
| *C11D 3/48* | (2006.01) | |
| *C02F 103/42* | (2006.01) | |

(52) U.S. Cl.
CPC ............ *C01B 11/024* (2013.01); *A01N 59/00* (2013.01); *B01J 19/00* (2013.01); *C01B 11/022* (2013.01); *C02F 1/76* (2013.01); *C02F 2103/42* (2013.01); *C02F 2303/02* (2013.01); *C02F 2303/04* (2013.01); *Y02W 10/37* (2015.05)

(58) Field of Classification Search
CPC ...... A01N 59/00; A01N 25/00; C01B 11/024; C01B 11/022; C02F 2303/04
See application file for complete search history.

(56) References Cited

U.S. PATENT DOCUMENTS

| | | | | |
|---|---|---|---|---|
| 2,323,593 | A * | 7/1943 | Hampel et al. | ............... 423/477 |
| 5,380,518 | A | 1/1995 | Roozdar | |
| 6,280,775 | B1 * | 8/2001 | Sasson et al. | ................ 424/616 |
| 6,428,696 | B2 | 8/2002 | Kuke | |
| 7,303,737 | B2 * | 12/2007 | Hemker | ................ C01B 11/024 |
| | | | | 423/477 |
| 2004/0022667 | A1 * | 2/2004 | Lee et al. | .......................... 422/4 |
| 2007/0116636 | A1 * | 5/2007 | Hemker et al. | ............... 423/477 |
| 2012/0148477 | A1 * | 6/2012 | Rosenblatt | ............ C01B 11/028 |
| | | | | 423/477 |

FOREIGN PATENT DOCUMENTS

| | | |
|---|---|---|
| CN | 2729037 Y | 9/2005 |
| DE | 834999 B | 7/1952 |
| DE | 858 998 C | 12/1952 |
| DE | 10 2006 060 578 A1 | 6/2008 |
| DE | 10 2006 060578 A1 | 6/2008 |
| JP | 03-285801 A | 12/1991 |
| JP | 09 202603 | 8/1997 |
| JP | 11 157805 | 6/1999 |
| RU | 45 378 U1 | 5/2005 |
| WO | 2005087657 A1 | 9/2005 |
| WO | 2006014719 A1 | 2/2006 |

OTHER PUBLICATIONS

Lenntech, "Disinfectants Chlorine Dioxide", http://www.lenntech.com/processes/disinfection/chemical/disinfectants-chlorine-dioxide.htm, Sep. 2009.*
"Herstellung von Reinem Chlordioxid IM Laboratorium", Unnwelt and Degussa. Produkte, Verfahren, Methoden, 1991, Seite Complete, XP000847684.
Chinese Office Action, issued in CN 201180062425.X on Nov. 28, 2014, English translation only, 6 pages.
Chinese Office Action issued in CN 201180062425.X on Aug. 14, 2015, 11 pages.
Notice of Allowance in Corresponding Russian Application No. 2013134256 dated Jun. 24, 2015, 9 pages.
Masayoshi Nakahara, "Muki kagoubutsu sakutai jiten [Dictionary of Inorganic Compounds & Complexes]", published by Kodansha Company Ltd., 1997, pp. 664-665.
Mitsumi Kaneko, "Suishitsu eiseigaku [Water Quality Hygiene]", published by Gihodo Shuppan Co., Ltd., 1996, pp. 312-314.
English translation of the Decision of Refusal dated Aug. 31, 2015, issued in the examination proceedings of the corresponding Japanese Application 2013-545112, 10 pages.
English translation of the summary of Mexican Office Action No. 74150 dated Oct. 3, 2016, 5 pages with translation.
English translation of Japanese Office Action in corresponding Japanese Pat. Appl. No. 2013-545112 dated Nov. 1, 2016, 9 pages.
Chinese Office Action issued in CN 201180062425.X on Mar. 28, 2016, 15 pages.
Australian First Examination issued in AU 2011348371 on Apr. 29, 2016, 4 pages.

* cited by examiner

Primary Examiner — Robert T Crow
Assistant Examiner — John P Nguyen
(74) Attorney, Agent, or Firm — Rothwell, Figg, Ernst & Manbeck, P.C.

(57) ABSTRACT

The invention relates to a method for producing an ultrapure, aqueous, long-term- and storage-stable, and thus transportable chlorine dioxide solution, comprising the steps of providing chlorite, providing peroxodisulfate, and combining chlorite and peroxodisulfate in an aqueous system and in a molar ratio of peroxodisulfate to chlorite $[S_2O_8^{2-}]/[ClO_2^-]$ of greater than 1, forming the aqueous chlorine dioxide solution, wherein no additional buffer is added to produce the aqueous chlorine dioxide solution. The invention further relates to a corresponding chlorine dioxide solution, to the use of said chlorine dioxide solution, and to a device for producing the chlorine dioxide solution.

12 Claims, 1 Drawing Sheet

METHOD FOR PRODUCING AN AQUEOUS STABLE CHLORINE DIOXIDE SOLUTION

This application is a 35 U.S.C. 371 National Phase Entry Application from PCT/EP2011/006510, filed Dec. 22, 2011, which claims the benefit of German Patent Application No. 10 201 0 055 982.2 filed on Dec. 23, 2011, the disclosures of which are incorporated herein in their entirety by reference.

The invention relates to a method for producing an ultrapure, aqueous, long-term- and storage-stable and therefore transportable chlorine dioxide solution, comprising the steps of providing chlorite, providing peroxodisulfate, and combining chlorite and peroxodisulfate in an aqueous system and in a molar ratio of peroxodisulfate to chlorite $[S_2O_8^{2-}]/[ClO_2^-]$ of greater than 1, forming the aqueous chlorine dioxide solution, wherein no additional buffer is added to produce the aqueous chlorine dioxide solution. The invention further relates to corresponding chlorine dioxide solutions, to the use of said chlorine dioxide solutions, and to a device for producing the chlorine dioxide solutions.

Because of the high oxidative power of the chlorine dioxide, aqueous solutions of chlorine dioxide ($ClO_2$) are used for bleaching, disinfecting and deodorizing, in particular in water treatment technology. However, chlorine dioxide solutions are generally considered difficult to handle because gaseous chlorine dioxide escapes easily from solutions and is explosive in higher concentrations. Therefore, chlorine dioxide solutions are generally not sold as finished solutions for the aforementioned applications, but rather prepared as needed onsite and then used.

Various methods are known for the production of aqueous chlorine dioxide solutions.

An aqueous chlorine dioxide solution can be generated, for example, by reacting a sodium chlorite solution with a hypochlorous acid solution (the so-called hydrochloric acid-chlorite-method). However, one of the disadvantages of this method is that the chlorine dioxide in that solution is not always stable and decomposes into chlorate and chloride within a short time. This is why solutions prepared in this way cannot be stored; they have to be used immediately.

With the so-called chlorine-chlorite-method, a sodium chlorite solution is reacted either with chlorine or with hypochlorous acid. This method, however, has the disadvantage that gaseous chlorine and hypochlorous acid is difficult to handle. In addition, a significant amount of chlorate is generated with this method as an undesired byproduct, which reduces the chlorine dioxide yield and therefore the oxidation power of the solution.

As an alternative to the two methods described above, it has been proposed to make a chlorine dioxide solution by oxidation of chlorite with peroxodisulfate. For example, WO-A-96/33947 describes a method for producing an aqueous chlorine dioxide solution, with a solution of chlorite being reacted with a halogen-free oxidizing agent at a pH value in the range of 5.5 to 9.5 at room temperature until the chlorite has been essentially completely converted to chlorine dioxide. Preferably, peroxodisulfate is used as oxidation agent, with said document—like the remaining prior art—describing the following summation equation (I) for the reaction of chlorite with peroxodisulfate:

$$2ClO_2^- + S_2O_8^{2-} \rightarrow 2ClO_2 + 2SO_4^{2-} \quad (1)$$

Proceeding from said summation equation, it is generally assumed that one equivalent of peroxodisulfate oxidizes two equivalents chlorite. Consequently, WO-A-96/33947 proposes to use peroxodisulfate in a quantity between one- or two times of the quantity required stoichiometrically for the oxidation of the chlorite. Therefore, WO-A-96/33947 describes a molar ratio of peroxodisulfate to chlorite $[S_2O_8^{2-}]/[ClO_2^-]$ in a range of 0.5 to 1.0.

A corresponding method is also described in U.S. Pat. No. 2,323,593, with the examples in said patent describing molar ratios of peroxodisulfate to chlorite $[S_2O_8^{2-}]/[ClO_2^-]$ of 0.57 and/or 0.78. Furthermore, U.S. Pat. No. 2,323,593 describes that peroxodisulfate to chlorite $[S_2O_8^{2-}]/[ClO_2^-]$ ratios of <0.5 are disadvantageous because they slow down the speed of the reaction.

EP-A-1 787 953 also describes a method for the production of chlorine dioxide solutions by reacting chlorite and peroxodisulfate, with the chlorine dioxide solutions being provided for the disinfection of skin or of hard surfaces. Therefore, EP-A-1 787 953 focuses on quickly providing extremely diluted chlorine dioxide solutions (2 to 300 ppm) at the particular point of use. To do so, a molar ratio of peroxodisulfate to chlorite $[S_2O_8^{2-}]/[ClO_2^-]$ of greater than 2 is used, with the peroxodisulfate solution as well as the chlorite solution being buffered.

However, the methods described above have a number of disadvantages that complicate their application.

In particular, the solutions have a short storage stability, which is maximally limited to only a few weeks, and therefore the application of aged solutions is problematic with respect to their active substances and decomposition products. Furthermore, a distribution of the finished solution is usually not possible. Therefore, production at the point of use is generally recommended (see, for example, EP-A-1 787 953). The production of the appropriate chlorine dioxide solution is up to the user, who must prepare the chlorine dioxide solution himself by mixing the appropriate preliminary solutions. This, however, requires technical knowledge with respect to determining the degree of conversion and the formation of byproducts.

Furthermore, the methods known from prior art have the disadvantage that temperatures above room temperature or alternately long reaction times are required for a controlled reaction. Also, other problems with the methods commonly used to date are systematically fluctuating, strongly temperature-dependent reaction times and yields, as well as the varying degrees of purity. Furthermore, the pH-value usually requires stabilization with various buffer systems as well as the addition of reaction accelerators (silver and copper salts, Caro's acid), which further reduce the purity of the chlorine dioxide solution to be used.

The present invention is therefore based on the problem of providing a chlorine dioxide solution with high storage stability, which does not necessarily have to be prepared at the point of use, but can also be sold as a ready-made solution. Furthermore, the present invention is based on the problem of providing a method for the production of said chlorine dioxide solutions, which allows the production of a stable chlorine dioxide solution in a simple manner under mild reaction conditions.

The object of the invention is attained with the embodiments characterized in the claims.

In particular, a method for the production of an aqueous chlorine dioxide solution is provided, which comprises the following steps:
(a) Providing chlorite;
(b) Providing peroxodisulfate;
(c) Combining chlorite and peroxodisulfate in an aqueous system and in a molar ratio of peroxodisulfate to chlorite $[S_2O_8^{2-}]/[ClO_2^-]$ of greater than 1 with the formation of the aqueous chlorine dioxide solution, with no additional buffer being added for the production of the aqueous chlorine dioxide solution.

The steps (a) and (b) can be performed in any desired order.

In step (a) of the method according to the invention, chlorite ($ClO_2^-$) is provided. According to the invention, chlorite can be used in form of the chlorous acid $HClO_2$ or as suitable salt. Preferably, the chlorites are selected from the group comprised of alkali metal chlorites, in particular lithium chlorite, sodium chlorite and potassium chlorite, alkaline earth metal chlorites, in particular magnesium chlorite and calcium chlorite, ammonium chlorites, in particular ammonium chlorite ($NH_4ClO_2$) and tetraalkyl ammonium chlorites such as tetramethyl ammonium chlorite, tetraethyl ammonium chlorite, and tetrabutyl ammonium chlorite, as well as mixtures thereof. Chlorite from the group comprised of sodium chlorite, potassium chlorite, and mixtures thereof is especially preferred.

Chlorite can be used either as a solid substance or in form of a solution, in particular in form of an aqueous solution. Preferably, chlorite is used in purest possible the purest possible form because in general, contaminations can interfere in the reaction of chlorite and peroxodisulfate into chlorine dioxide and decrease the stability of the resulting chlorine dioxide. Nevertheless, it is also possible to use solid sodium chlorite, which is commercially available and, in addition to sodium chlorite, may contain up to 25 percent by weight [wt %] sodium chloride, preferably up to about 20 wt % sodium chloride, especially preferably up to about 10 wt % sodium chloride, because sodium chloride does not interfere with the reaction yielding chlorine dioxide, nor does it interfere with the stability of the chlorine dioxide. In a preferred embodiment of the method according to the invention, chlorite is provided in solid form as molded piece, tablet, capsule or pellet.

In step (b) of the method according to the invention, peroxodisulfate ($S_2O_8^{2-}$) is provided. According to the invention, peroxodisulfate can be used in form of the peroxydisulfuric acid $H_2S_2O_8$ or as a suitable salt. Preferably, the peroxodisulfates are selected from the group comprised of alkali metal peroxodisulfates, in particular lithium peroxodisulfate, sodium peroxodisulfate and potassium peroxodisulfate; alkaline earth metal peroxodisulfates, in particular magnesium peroxodisulfate and calcium peroxodisulfate; ammonium peroxodisulfates, in particular ammonium peroxodisulfate (($NH_4)_2S_2O_8$); and tetraalkyl ammonium peroxodisulfates such as tetramethyl ammonium peroxodisulfate, tetraethyl ammonium peroxodisulfate and tetrabutyl ammonium peroxodisulfate, as well as mixtures thereof. Peroxodisulfate from the group comprised of sodium peroxodisulfate, potassium peroxodisulfate, and mixtures thereof is especially preferred.

Peroxodisulfate can be used either as solid substance or in form of a solution, in particular in form of an aqueous solution. Preferably, peroxodisulfate is used in purest possible form because in general, contaminants can interfere in the reaction of chlorite and peroxodisulfate into chlorine dioxide and reduce the stability of the resulting chlorine dioxide. In a preferred embodiment of the method according to the invention, peroxodisulfate is provided in solid form as molded piece, tablet, capsule or pellet.

Furthermore, it is also possible to provide chlorite and peroxodisulfate together, for example as a two-phased binary solids mixture or as a molded piece, tablet, capsule or pellet, which contains one or both components separately and with time-delayed dissolution.

If chlorite and/or peroxodisulfate are provided in form of a solution, it is preferably in form of an aqueous solution. Any suitable water, such as tap water, for example, can be used as solvent. However, purified or distilled water is used preferably. The aqueous solutions can also contain additional suitable co-solvents such as halogenated or non-halogenated organic solvents, for example. In a preferred embodiment, the additional solvent is suitable solvent that is inert, miscible with water, suitable with respect to reaction, and preferably selected from the group comprised of methanol, ethanol, n-propanol, iso-propanol, butanol and mixtures thereof. It is especially preferred to use a solvent that can be mixed with water. For example, the additional solvent can be used in a quantity of up to 80 percent by volume [pbv], preferably up to 50 pbv, especially preferred up to 10 pbv, and very especially preferred up to 5 pbv.

Step (c) of the method according to the invention comprises combining chlorite and peroxodisulfate in an aqueous system with the formation of the aqueous chlorine dioxide solution. Said combining can be done using all suitable methods known from prior art. Preferably, the two components are combined with mixing. The mixing can also be done using all suitable methods known to a person skilled in the art. For example, the mixing can be done on the laboratory scale using a laboratory stirrer. On the industrial scale, for example, the mixing can be performed in a stirred tank. Preferably, combining is performed in such a way that it results in a homogenous solution of the two components, which essentially no longer includes any solid matter. Mixing with the help of a mixing device offers the advantage that it speeds up the reaction of chlorite and peroxodisulfate into chlorine dioxide.

In a preferred embodiment of the method according to the invention, chlorite and peroxodisulfate are provided in solid form in steps (a) and (b) or in an aqueous solution, wherein in step (c)

(c1) both components are dissolved in water before being combined, if both components are provided in solid form, or (c2) both components are introduced in solid form into an aqueous solvent at the same time or successively, or (c3) both solutions are combined if both components are provided in form of aqueous solutions, or (c4) both components are provided in aqueous solution and introduced into an aqueous solvent at the same time or successively to produce the aqueous chlorine dioxide solution.

Preferably, the combining is done in step (c1) by dissolving both components together in water, at the same time or successively, if both components are provided in solid form. If chlorite and peroxodisulfate are provided as a binary solids mixture or as a molded piece, for example, said solids mixture or said molded piece can be simply dissolved in water and then the two solutions obtained in this way can be combined in the molar ratio essentially at the same time or also successively.

In step (c2), the two components are preferably introduced successively in solid form into an aqueous solvent. In particular, it is preferred in that case to first place the peroxodisulfate into an aqueous solution and then add chlorite, either in solid form or in aqueous solution.

In step (c3), both solutions are preferably combined at the same time in the molar ratio according to the invention. However, it is also possible to first prepare the aqueous solution with peroxodisulfate and then add the chlorite solution.

In step (c4), the two components are preferably provided in aqueous solution and introduced successively into an aqueous solvent. In that case, the order of addition is not important and either the aqueous peroxodisulfate solution or the chlorite solution can be added first, and then the respective other solution is added.

The preferred method is the method according to (c3), with both components first being dissolved separately in an aqueous solvent; then the two solutions are combined and mixed.

It is especially preferred to add an aqueous solvent, especially preferred purified or distilled water, in the desired quantity and then remove the quantities desired for the production of the aqueous solution of the two components, produce the solutions, and then add them back to the aqueous solvent.

In all cases (c1) to (c4), the aqueous solutions can include chlorite in any suitable concentration up to the saturation concentration of the corresponding chlorite salt. The respective saturation concentration does not represent a firm value but depends, for example, on the temperature used and nature of the specific chlorite salt. For example, sodium chlorite has a saturation concentration of about 64.5 wt % at 20° C. However, it is preferred to adjust the concentration of the aqueous chlorite solutions to no more than about 5 wt %, preferably no more than 2 wt %, and especially preferably to no more than 1 wt %. The peroxodisulfate concentration in the aqueous solution can be up to its saturation concentration. The respective saturation concentration does not represent a firm value but depends, for example, on the temperature used and the type of the specific peroxodisulfate salt. For example, sodium peroxodisulfate has a saturation concentration of about 54.5 wt % at 20° C.

The water used to prepare the chlorine dioxide solution according to the invention can be any suitable water, such as tap water, for example. Preferably, however, purified or distilled water is used because in this way, the solution contains less foreign matter, which is advantageous with respect to a better reaction of chlorite and peroxodisulfate into chlorine dioxide and an increased stability of the chlorine dioxide obtained in this manner. Furthermore, one of the co-solvents described above can also be used in the preferred quantities described above.

After chlorite and peroxodisulfate are combined, chlorine dioxide is formed. Because this reaction is performed in an aqueous system, the resulting chlorine dioxide is present in the form of an aqueous solution.

After the chlorine dioxide has been produced into aqueous solution, it is also possible to add solvents that are not miscible with water, such as organic solvents, in particular dichloromethane, chloroform and/or tetrachloromethane, and convert chlorine dioxide into the organic phase. This leads to more stable solutions of chlorine dioxide in organic solvents.

Surprisingly, it was found that in said reaction, contrary to the summation equation (I) described above, an equivalent of peroxodisulfate reacts with an equivalent of chlorite and forms a stable chlorine dioxide solution when adhering to the molar ratios of peroxodisulfate to chlorite of greater than 1 according to the invention. It is assumed, without being tied to any theory, that in this reaction, a hydrogen sulfate radical is formed, which exercises a stabilizing effect on the formed chlorine dioxide. This reaction is shown by the following summation equation (2):

$$ClO_2^- + HS_2O_8^- \rightarrow [ClO_2^\cdot . HSO_4^\cdot] + SO_4^{2-} \quad (2)$$

In this reaction, $HS_2O_8^-$ is formed autocatalytically from $S_2O_8^{2-}$. In the reaction of a chlorite equivalent and a peroxodisulfate equivalent, consequently a hydrogen sulfate radical $HSO_4^\cdot$ is formed in addition to a chorine dioxide radical $ClO_2^\cdot$. These two radicals stabilize each other by association, with is represented by the radical pair $[ClO_2^\cdot . HSO_4^\cdot]$. This representation is only exemplary. It is also conceivable that such a radical pair forms an association with water in the form $[ClO_2^\cdot . H_2O . HSO_4^\cdot .]$. The hydrogen sulfate radical as such has not been considered stable to date.

It is furthermore assumed, without being tied to a theory, that the stabilization of the radical complex $[ClO_2^\cdot . HSO_4^\cdot]$ can be supported with the following observations:

1) Because of the proton of the hydrogen sulfate radical, the chlorine dioxide solution has an acidic pH-value (preferably in the pH-range of 2.5 to 3). Therefore, each chlorine dioxide radical is in a weakly acidic milieu and it is assumed that this contributes to the stabilization of the chlorine dioxide radical.
2) The association with the hydrogen sulfate radical could lead to a strengthening of the hydrate formation, which would increase the water solubility. Furthermore, the vapor pressure of the radical could be reduced because of the association.
3) The association possibly also reduces the reconversion tendency of the chlorine dioxide radical into chlorite.
4) It is assumed that because of the uncharged nature of both radicals in the associate, there is no effect with respect to its mobility and/or permeability through otherwise salt-impermeable membranes such as reverse osmosis membrane (RO), nanofiltration membranes, etc.
5) Furthermore, it is assumed that the hydrogen sulfate radical can possibly react with water, giving hydrogen monopersulfate or hydrogen sulfate and/or sulfate. In this reaction, chlorine dioxide reacts to form chlorite or chlorate. Consequently, the decomposition of the radical complex $[ClO_2^\cdot . HSO_4^\cdot]$ leads to decomposition products in a safe manner. In oxidation reactions, the radical complex reacts by forming the environmentally irrelevant anions chloride and sulfate. Contrary to this, conventional, i.e. non-stabilized chlorine dioxide solutions, tend decompose explosively because of the formation of chlorine and oxygen.
6) The chlorine dioxide radical concentration is the variable that determines the formation of the radical pair.

The formation of the radical pair associate described above has been verified with experimental studies that show that said radical pair associate is distilled as a whole and therefore can enter into the gaseous phase; it is also membrane-permeable. Furthermore, compared to the chlorine dioxide radical, the radical pair associate $[ClO_2^\cdot . HSO_4^\cdot]$ has different physical properties, such as, for example, a different vapor pressure and a different solubility. The oxidation potential of the hydrogen sulfate radical is completely available as oxidation potential with an additional electron equivalent and there is therefore no loss of oxidation potential. This has been verified by means of photometry and titration. Overall, six electron equivalents are available; five for the reduction of chlorine dioxide into chloride and one for the reduction of the hydrogen sulfate radical into sulfate. Studies have shown that in water, first the chlorine dioxide radical is removed by reaction, and only thereafter the hydrogen sulfate radical.

In view of the findings described above, the method according to the invention is characterized in that, compared to the methods known from prior art, it proceeds from a different stoichiometry for the reaction of chlorite and peroxodisulfate into chlorine dioxide.

Therefore, in step (c) of the method according to the invention, chlorite and peroxodisulfate are used in a molar ratio of peroxodisulfate to chlorite $[S_2O_8^{2-}]/[ClO_2^-]$ of greater than 1. This means that an equivalent chlorite is reacted with a molar excess of peroxodisulfate, whereas with the conventional methods, generally only about 0.5 equivalents peroxodisulfate were used for one equivalent chlorite.

In a preferred embodiment of the present invention, the starting materials are used in a molar ratio of peroxodisulfate to chlorite between 1 and 2 ($1<[S_2O_8^{2-}]/[ClO_2^-]<2$). Only a slight excess of peroxodisulfate is used with respect to chlorite, which means that with complete reaction of the chlorite, less than one equivalent of non-reacted peroxodisulfate (with respect to the chlorine dioxide formed) remains in the chlorine dioxide solution. Because the presence of additional components generally decreases the stability of the chlorine dioxide in the solution (even if only to a slight extent by the peroxodisulfate), the molar ratio between 1 and 2 described above leads to a chlorine dioxide solution with an increased stability.

In another preferred embodiment of the present invention, the starting materials are used in a peroxodisulfate to chlorite molar ratio of greater than 2, especially preferred of greater than 4, even more especially preferred of greater than 10. Furthermore, it is possible to use a peroxodisulfate to chlorite ratio of up to about 100. In that embodiment, a greater excess of peroxodisulfate is used with respect to chlorite to obtain a quicker and/or more complete reaction of the chlorite into chlorine dioxide.

By adhering to the molar ratios according to the invention, the reaction proceeds faster and almost quantitatively. In the method according to the invention, a yield of more than about 80% is especially preferred, especially more than about 90% and very especially more than 95% relative to the quantity of chlorite used. No secondary reactions are observed with the reaction conditions according to the invention.

Furthermore, it was found that for an effective reaction of chlorite and peroxodisulfate into chlorine dioxide, it is no longer necessary to adjust the reaction solution to a specific pH-value by adding a buffer. Rather, it was found that by adding a buffer, additional foreign matter is introduced into the aqueous solution, which decreases the reaction speed into chlorine dioxide and the stability of the chlorine dioxide in the solution. Accordingly, according to the invention, no buffer is added in the production of the aqueous chlorine dioxide solution, i.e., no additional buffer is added in the production. However, this does not mean that the resulting solution does not contain a buffer. For example, a hydrogen sulfate/sulfate buffer can form from the sulfate formed during the reaction.

A commonly used buffer for the stabilization of chlorine dioxide is a substance mixture of at least one weak acid and its conjugated base. Weak acids in terms of the present invention are acids with a $pK_a$ value of about −2 to about 12 in water. By adding a buffer, the pH-value of an aqueous solution is essentially kept constant within a pH-range. Therefore, each buffer system has a pH-range within which the pH-value does not change significantly if a strong acid is added. Strong acids are acids that are present completely dissociated in aqueous solution.

In particular, according to the invention, no buffer selected from the group consisting of an acetate buffer, a phosphate buffer, a borate buffer, a citrate buffer and a carbonate buffer is used. In particular, according to the invention, no hydrogen carbonate or carbonate is used.

Especially preferred, to an aqueous chlorite solution provided in step (a), no buffer is added that would buffer the solution in a pH-range of 9 to 12. Also, preferably no buffer that buffers the solution in a pH-range of 3 to 9 is added to an aqueous peroxide sulfate solution provided in step (b).

In a preferred embodiment of the present invention, the chlorine dioxide solution is produced in that a solution of chlorite is combined with a solution of peroxodisulfate. Preferably, the peroxodisulfate solution is used in a concentration so that it has a pH-value in the range of about 4 to about 8. In a preferred embodiment, the pH-value of the peroxodisulfate solution is about 4 to about 6, in another preferred embodiment the pH-value is about 6 to about 8. Furthermore, the chlorite solution is preferably used in a concentration that it has a pH-value in the range of about 10 to about 12. Especially preferred, the peroxodisulfate solution has a pH-value of about 5 and the chlorite solution has a pH-value of about 11.

If the aqueous solutions of chlorite and peroxodisulfate described above are combined, the pH-value of the solution preferably adjusts to a value of about 2 to about 4 during the reaction of chlorite and peroxodisulfate into chlorine dioxide, i.e. as the reaction of chlorite and peroxodisulfate into chlorine dioxide nears completion, the pH-value of the aqueous solution stabilizes to a range of about 2 to about 4. It is especially preferred if the pH-value adjusts to a range of about 2.5 to about 3. Even more preferred, chlorite and peroxodisulfate are used in a quantity and concentration that the pH-value of the combined solution stabilizes to a value of about 2.5 during the reaction.

A buffer can be added to the resulting chlorine dioxide solutions after their production; preferably a buffer that buffers in a pH-range of about 2 to 4.

The method according to the invention can be performed at any suitable temperature. However, it is advantageous if the reaction of chlorite and peroxodisulfate is performed at relatively low temperatures in the range of about 0° C. to about 25° C. In contrast to this, the conventional methods generally require higher temperatures above 25° C. to achieve an accelerated reaction of chlorite and peroxodisulfate into chlorine dioxide. In a preferred embodiment of the present invention, the peroxodisulfate and chlorite are combined at a temperature in the range of about 0° C. to about 25° C., especially preferred in a range of about 2° C. to about 20° C. Especially preferred, the step (c) of combining is performed at a temperature in the range of about 5° C. to about 15° C. It was shown that at higher temperatures (i.e., temperatures greater than 25° C.), secondary reactions occur, which lead to undesired byproducts. The formation of byproducts is a disadvantage because they reduce the stability of the chlorine dioxide solution according to the invention.

It is furthermore advantageous that said temperature range is not only maintained during the combining of the chlorite component and the peroxodisulfate component, but rather long enough until the reaction of chlorite and peroxodisulfate into chlorine dioxide is essentially completed. To do so, the respective aqueous solutions are preferably brought to the appropriate temperature before the combining and then kept in that temperature range long enough until the reaction into chlorine dioxide is essentially completed. In addition to the tempering of the solutions, it is furthermore advantageous to temper the environment to the preferred temperature ranges described above during the combining and until the reaction is completed. This can be done, for example, in a refrigerator, cold storage or a cooling container. In an especially preferred embodiment of the method according to the invention, a chlorite solution and a peroxodisulfate solution are combined with cooling at a temperature in the range of about 5° C. to about 15° C. and then left to react in said temperature range until the reaction into chlorine dioxide is completed.

In another preferred embodiment, the chlorine dioxide solution obtained with the method according to the invention is kept and/or stored at said temperature range even after the reaction is completed. Pure chlorine dioxide has a boiling point of 11° C. at 1013 mbar. Preferably, the aqueous chlorine dioxide solution obtained with the method according to the invention is therefore stored below about 11° C., in particular at a temperature in the range of about 0° C. to about 11° C.

If the combining of chlorite and peroxodisulfate is performed in the preferred temperature range of about 0° C. to about 25° C., preferably greater than 0° C. to about 11° C., the appearance of secondary reactions and therefore of undesired byproducts such as chlorine, hypochlorite and chlorate can be essentially avoided during the formation of chlorine dioxide. Therefore, the chlorine dioxide solution prepared according to the invention includes less foreign matter, which further increases the stability of the chlorine dioxide solution according to the invention.

Preferably, the method according to the invention is performed in the dark. It has been found, for example, that the formation of byproducts is possible in the presence of UV radiation and/or sunlight. The formation of byproducts is disadvantageous because it has been found that byproducts and/or foreign matter destabilize the chlorine dioxide solution. The less byproducts there are in the reaction mixture, the greater is the long-term stability of the obtained solution.

The combining of chlorite and peroxodisulfate in step (c) of the method according to the invention leads to a reaction between these two components, and chlorine dioxide is formed (see summation equation (2) above). With the method according to the invention, it is possible to obtain a nearly quantitative reaction (i.e. a reaction of greater than 95%) of chlorite into chlorine dioxide within about 72 hours. Preferably, the nearly quantitative reaction is already obtained after 48 hours, especially preferably already after 24 hours. Especially for 0.3 to 0.6 wt % solutions, a nearly quantitative reaction is obtained already after about 48 hours, preferably already after 24 hours. For solutions of higher concentration (for example, concentrations of 1 wt % or more), the reaction time can be reduced to a few minutes until a quantitative reaction is obtained, preferably to 30 minutes or less, especially preferably to 15 minutes or less. With constant temperature and constant peroxodisulfate-chlorite ratio, the reaction rate increases commensurate with the chlorite concentration, i.e., the higher the chlorite concentration, the quicker the reaction. At a constant concentration of chlorite and peroxodisulfate, the conversion rate increases commensurate with the temperature, i.e. the higher the temperature the quicker the reaction. Finally, an increase of the ratio of peroxodisulfate to chlorite at constant temperature also leads to a quicker reaction.

The prior art, on the other hand (see, for example, WO-A-96/33947) describes reaction times of about 12 days until the quantitative reaction for the production of highly concentrated chlorine dioxide solutions.

Preferably, the method according to the invention includes according to step (c) the additional step of letting chlorite react with peroxodisulfate until chlorite has been essentially completely converted (i.e. more than 95% of the chlorite used) into chlorine dioxide. In an especially preferred embodiment, the method according to the invention includes according to step (c) the additional step of letting the chlorite react with peroxodisulfate for a period of 12 hours, preferably for a period of at least 24 hours, and even more preferably for a period of at least 36 hours. In another especially preferred embodiment, the method according to the invention includes according to step (c) the additional step of letting chlorite react with peroxodisulfate for a period of 12 to 48 hours and preferably for a period of 24 to 36 hours.

With the method according to the invention, chlorine dioxide solutions can be produced in any desired and/or suitable concentration. Preferably, aqueous solutions of up to about 2 wt %, preferably about 1 wt % of chlorine dioxide are produced with the method according to the invention. Chlorine dioxide solutions with higher concentrations are more difficult to obtain because of the limited solubility of chlorine dioxide in water, but they can nevertheless be realized. When using higher concentrations of chlorite for the production of the chlorine dioxide solutions according to the invention, in particular when using chlorite concentrations in the range of the saturation solubility of the corresponding chlorite salt, aqueous chlorine dioxide solutions with a concentration of up to about 4.5 wt % can be produced. The value of about 4.5 wt % represents the saturation limit of chlorine dioxide in water determined experimentally at 5° C. and normal pressure. With higher pressure, even free chlorine dioxide phases can be generated in water. Such mixtures typically contain more than about 4.5 to about 12 wt % chlorine dioxide relative to the total amount of chlorine dioxide and water because the solubility of chlorine dioxide in water is influenced significantly by foreign matter dissolved in water, which reduces the solubility of the chlorine dioxide. This means that the solubility of chlorine dioxide is higher, the less foreign matter there is in the solution. Because chlorine dioxide solutions with a lower foreign matter portion can be obtained with the method according to the invention, the solubility of chlorine dioxide in the solutions according to the invention is higher than in conventional chlorine dioxide solutions.

Furthermore, even at relatively high concentrations of up to about 12 wt %, and preferably of up to about 2 wt % of chlorine dioxide, the chlorine dioxide solutions according to the invention are easy to handle and do not exhibit any tendency toward explosion due to spontaneous decomposition. However, with the method according to the invention, as a precaution, preferably chlorine dioxide solutions with a concentration of up to about 2.5 wt %, especially preferred up to about 1 wt %, and very especially about 0.6 wt % chlorine dioxide are produced for safety reasons. The prior art, on the other hand, describes that chlorine dioxide solutions are more stable if they are present in diluted form. Therefore, the prior art mostly describes concentrations of no more than 0.3 wt %. However, it goes without saying that it is also possible with the method according to the invention to produce less concentrated solutions of chlorine dioxide, if so desired. This can also be done, for example, by first using the method according to the invention to produce higher concentrated solutions of chlorine dioxide with concentrations preferably in the range of about 0.5 to about 4.5 wt %, and then diluting them to the desired lower concentrations, for example in the range of about 0.003 to about 1 wt %.

Therefore, preferably solutions with a chlorine dioxide concentration in the range of 0.003 wt % to about 4.5 wt %, more preferred in the range of about 0.03 wt % to about 2.5 wt %, and even more preferred in the range of about 0.1 wt % to 1 wt %, and especially preferred in the range of more than about 0.3 wt % to about 0.6 wt % and especially of about 0.5 wt % to about 0.6 wt % are produced in the scope of the present invention. Corresponding solutions with a chlorine dioxide concentration of more than about 0.3 wt % to about 0.6 wt % are especially advantageous because they are clearly more concentrated than conventional chlorine dioxide solutions and are nevertheless storage stable and handle well. The suitable concentration depends significantly on the intended use and can be selected accordingly by a person skilled in the art. Less concentrated solutions can also be readily obtained from higher concentrated chlorine dioxide solutions with appropriate dilution, as described above.

With the method according to the invention, chlorine dioxide can be produced either continually in continuous operation or in batches in batch operation. If the method according to the invention is performed in continuous operation, it is especially advantageous to provide chlorite as well as peroxodisulfate in form of aqueous solutions.

In another preferred embodiment of the present invention, the solution obtained after the combining in step (c) is filled into a container in which the solution can be stored and/or transported. The conversion into chlorine dioxide does not have to be completed when the solution is filled into the container. That is because it is also possible for the completion of the reaction from chlorite and peroxodisulfate into chlorine dioxide to occur after the solution has been filled into the container designated for storage or transport of the solution. Therefore, the filling step can occur before or after the optional additional step of letting the chlorite react with peroxodisulfate. In another preferred embodiment, the combining in step (c) occurs already in the container designated for the storage or transport of the solution. This variant is especially advantageous because it does not require another transfer of the finished chlorine dioxide solution. Suitable containers are described in the following.

The method according to the invention for the production of a chlorine dioxide solution and the chlorine dioxide solutions that can be obtained from it have many advantages compared to the prior art. For example, the method according to the invention facilitates the production of a chlorine dioxide solution under very mild reaction conditions (especially at a low temperature) using only two components. Furthermore, it requires only a small effort with respect to apparatus because heating the reaction mixture, for example, is not necessary. Furthermore, with the method according to the invention, a nearly quantitative conversion of the chlorine component is possible in relatively short reaction times without having to add an activator or catalyst (usually heavy metal salts) or using a defined buffer system.

Because of the simple and complete conversion, the resulting solution consists almost completely of chlorine dioxide and contains hardly any other components or foreign matter (such as, for example, unreacted starting materials, undesired byproducts, buffers, activators or catalysts), but almost solely $ClO_2$. Surprisingly, it has now been found that said absence of foreign matter in the chlorine dioxide solution significantly improves the stability of the chlorine dioxide solution. It has been found, for example, that the stability of the chlorine dioxide solution is higher, and the decomposition tendency of the chlorine dioxide solution is lower in inverse proportion to the purity of the chlorine dioxide solution. It follows from this that an increased stability of a chlorine dioxide solution is obtained if the chlorine dioxide is produced using as few chemicals as possible, which is made possible by the method according to the invention. It has been found that the additives apparently lead to the destabilization of the solution.

Because of the very selective conversion, the chlorine dioxide solution according to the invention contains only very small amounts, if any, of hypochlorite, chlorine and chlorate as foreign matter. Therefore, the risk of a decomposition of the chlorine dioxide due to possible redux reactions with said components is reduced significantly. Because of this, the chlorine dioxide solution according to the invention is stable in storage, especially for at least one year, without noticing a decomposition of the chlorine dioxide worth mentioning. Therefore, it is not necessary to add a stabilizer to the chlorine dioxide solution according to the invention.

To ensure an increased purity of the chlorine dioxide solution, no buffer is used for the production of the chlorine dioxide solution with the method according to the invention. Furthermore, in a preferred embodiment, the method according to the invention is limited to the use of the chlorite component as well as the peroxodisulfate component, with no additional components, selected from the group consisting of activators, catalysts and stabilizers being used for the production of the chlorine dioxide solution, i.e. added to the starting materials or added to the resulting chlorine dioxide solution. Activators may be radical initiators, for example. In an especially preferred embodiment, no catalysts whatsoever are used with the method according to the invention. Catalysts may be especially conversion metal salts such as, for example, silver-, manganese-, copper- and iron salts, or alkaline- and alkaline earth halides. In particular, it has been shown that the addition of alkali- and alkaline earth bromides and -iodides is disadvantageous because they lead to the destruction of the chlorine dioxide via the formation of bromide and iodide. Stabilizers can be EDTA salts, for example. In another preferred embodiment, no auxiliary substances, such as sorbitol, starch, polyethylene glycol, sodium benzoate or fragrances are used with the method according to the invention. In an especially preferred embodiment of the method according to the invention, the method is furthermore limited to the use of the chlorite component as well as the peroxodisulfate component, with no additional components being used for the production of the chlorine dioxide solution.

The prior art, on the other hand, describes that only high concentrations of chlorine dioxide accelerate the decomposition, and that the addition of buffers and/or stabilizers is required to increase the stability. It has now been possible to disprove this prejudice.

Because of said increased stability, the chlorine dioxide solutions according to the invention cannot only be stored on a long-term basis, but they also offer a transportable solution. Compared to the prior art, it is no longer required with the method according to the invention to produce the chlorine dioxide solution onsite immediately prior to the planned use. Rather, a chlorine dioxide solution can now also be produced and bottled in larger quantities, and only thereafter transported to the intended application site.

Furthermore, an application of the method according to the invention is possible without problems or risk on any scale, i.e. quantities in the milligram range up to large-scale applications in the range of several thousand cubic meters.

The solution is ready to use as soon as the production process according to the invention is completed and a further processing, for example with absorption columns, desalination [OR: desalting], mixing with other solutions, etc. is not necessary.

The present invention furthermore relates to an aqueous chlorine dioxide solution that is produced with the method described above.

The present invention furthermore relates to an aqueous chlorine dioxide solution that contains chlorine dioxide in a quantity of about 0.1 wt % to about 12 wt % and preferably of about 0.3 wt % to about 4.5 wt %, with the pH-value of the aqueous solution being in a range of about 2 to about 4 and the solution not containing a buffer. In an especially preferred embodiment, the aqueous solution contains chlorine dioxide in a quantity of about 0.3 to about 1 wt %, with the pH-value of the solution being in the range of about 2 to about 4 and the solution not containing a buffer. Even more preferred is a chlorine dioxide solution with a chlorine dioxide concentration in the range of more than about 0.3 to about 0.6 wt %. The solution according to the invention is especially advantageous because it is clearly more concentrated than conventional chlorine dioxide solutions and is nevertheless storage-stable and handles well.

The present invention furthermore relates to an aqueous chlorine dioxide solution that contains chlorine dioxide together with the hydrogen sulfate radical in form of a radical pair associate, with the solution not including a buffer. In a preferred embodiment, said chlorine dioxide solution according to the invention does not contain any additional components selected from the group consisting of activators, catalysts and stabilizers.

Said chlorine dioxide solutions have the aforementioned advantages of increased stability even at high concentrations and the related longer storability and transportability.

Because of their only weakly acid pH-value, the chlorine dioxide solutions according to the invention are furthermore low in corrosion and compared to conventional chlorine dioxide solutions, they have additional oxidation potential to protect the solution due to the additional hydrogen sulfate radical in the solution (see the summation equation (2) above) or a reaction product resulting from it.

The chlorine dioxide solutions according to the invention are stable and last or can be stored for at least one year, i.e., no significant decomposition of the chlorine dioxide solutions is observed during that period. Preferably, the chlorine dioxide solutions according to the invention can be stored indefinitely. To increase the storage stability of the chlorine dioxide solutions according to the invention, they are preferably stored cool, preferably at a temperature in the range of greater than 0° C. to about 25° C., especially preferably in a range of about 2° C. to about 20° C. and very especially preferred in a range of about 5° C. to about 15° C.

Furthermore, it is advantageous that the chlorine dioxide solutions according to the invention are stored in the dark. However, because it was surprisingly found that chlorine dioxide in aqueous solution is clearly more stable against UV radiation and/or sunlight than in the gaseous phase, it is sufficient, according to a preferred embodiment of the invention, to protect the gaseous phase above the solution from sunlight in the container in which the solutions are stored. For this purpose, a light-impermeable foil or a light-impermeable container and/or a opaque barrel can be used.

The aqueous chlorine dioxide solutions according to the invention are genuine solutions of chlorine dioxide in water, in which the chlorine dioxide does not hydrolyze. The vapor pressure of the solution is governed by Henry's law; i.e. the total of the partial pressures results in the total pressure. The vapor pressure of the chlorine dioxide is a function of the temperature and increases as the temperature increases. Chlorine dioxide in pure, non-aqueous form has a boiling point of 11° C. at 1013 mbar. In water, chlorine dioxide is soluble in surprisingly high concentrations without reacting with water. As the ambient temperature increases, the water solubility decreases and in the gaseous phase, chlorine dioxide behaves increasingly like an ideal gas, with the chlorine dioxide behaving even more real in the gaseous phase above the aqueous chlorine dioxide solution as the ambient temperature approaches the boiling point or even falls below said boiling point.

However, for various reasons, it is desirable to keep the vapor pressure of the chlorine dioxide solutions according to the invention as low as possible. That is because a chlorine dioxide vapor pressure causes part of the chlorine dioxide to escape from the solution, which decreases the concentration of useable chlorine dioxide. This can lead in particular to a significant loss of chlorine dioxide if the storage container for the chlorine dioxide solution according to the invention is aerated or open, for example. In this way, the chlorine dioxide can convert gradually from the solution into the gaseous phase and then escape from the container. Furthermore, the chlorine dioxide is less stable against UV radiation and/or sunlight in the gaseous phase than in dissolved form. Consequently, an increasing portion of chlorine dioxide in the gaseous phase can lead to increased decomposition reactions, which reduces the concentration and the purity of the chlorine dioxide in the solution according to the invention. Furthermore, the chlorine dioxide is clearly more dangerous and difficult to handle in the gaseous phase because of the explosive tendency.

Therefore, it is advantageous to store the aqueous chlorine dioxide solutions according to the invention below their boiling temperature of 11° C., in particular at a temperature in the range of greater than 0° C. to 11° C., and especially preferred at a temperature in the range of 5° C. to 11° C.

But the use of an overpressure is also advantageous with respect to reducing the vapor pressure of chlorine dioxide. For example, an overpressure of about 0.01 to about 10 bar, if applicable under inert gases such as nitrogen or the like, preferably in a range of about 0.1 to about 1 bar, can be applied to the chlorine dioxide solution according to the invention, which further reduces the vapor pressure of chlorine dioxide. But overpressures at temperatures above the boiling point lead to a similar result. Therefore, the solutions according to the invention can also be stored at temperatures of up to 40° C. if a suitable overpressure is applied to the solutions at the same time to reduce the chlorine dioxide quantity in the gaseous phase.

Therefore, according to the invention, it turned out that chlorine dioxide solutions—the ones according to the invention as well as conventional ones—can be advantageously stored in a container under pressure. The pressure is preferably 0.01 to about 10 bar, preferably in the range of about 0.1 to about 1 bar.

In an especially preferred embodiment of the chlorine dioxide solutions according to the invention, they are stored at a temperature in a range of greater than 0° C. to about 15° C. with simultaneous application of pressure in a range of about 0.1 bar to about 1 bar.

In another preferred embodiment of the present invention, the chlorine dioxide solutions can also be stored under an inert gas atmosphere.

Suitable containers, for example, are all conventional plastic or metal canisters, snap lid bottles, vats, glass bottles and the like. There are no limitations whatsoever with respect to the material as long as the material is inert relative to the chlorine dioxide and maximally corrosion-resistant. Preferably, glass-, metal- or plastic containers, especially of HDPE, LDPE, PVC, PTFE or copolymers are used. In a preferred embodiment of the present invention, the container provided for the mixing, transport and/or storage of the solutions is impermeable to light.

With respect to the containers for storing the chlorine dioxide solutions according to the invention, Henry's law should again be observed, which describes the temperature-dependent conditions of the solubility of chlorine dioxide in the gaseous phase and in the liquid after reaching equilibrium. In particular, purely mathematically, there is more chlorine dioxide in the container in the gaseous phase than in the liquid when the filling level is low. This also generally explains the main losses of active substance in chlorine dioxide solutions. Leaks in the storage containers lead to a continuous readjustment of the equilibrium and therefore to the complete loss of the active substance. The rate of equilibration also depends on the existing surface, with the conversion of the chlorine dioxide from the liquid into the gaseous phase depending on the surface of the solution and in particular the free gas space above it. If the surface of an otherwise closed container is covered, for example by a more or less tightly placed floating body, the rate of adjustment of the equilibrium of the chlorine dioxide in the gaseous phase to liquid is reduced significantly. Therefore, the container provided for the storage and/or transport of the solution according to the invention preferably has a floating body. In this way, it is possible to reduce the surface of the chlorine dioxide solution far enough at low filling levels that the vapor pressure of the chlorine dioxide remains low and the residual filling can also be used safely.

The pH-value of the chlorine dioxide solutions according to the invention is in a range of about 2 to about 4 and preferably in a range of about 2.5 to 3 in one embodiment. Said pH-value is in particular advantageous with respect to the stability of the solution according to the invention. Conventional chlorine dioxide solutions, on the other hand, generally have a pH-value of greater than 4, with said pH-value being achieved with a suitable buffer system. According to one embodiment of the present invention, said chlorine dioxide solution does not include a buffer. In a preferred embodiment, said chlorine dioxide solution according to the invention does not include any additional components selected from the group consisting of activators, catalysts and stabilizers.

In another embodiment of the chlorine dioxide solution according to the invention, said chlorine dioxide solution includes at least on additional radical in addition to chlorine dioxide. Preferably, said chlorine dioxide solution according to the invention is prepared with the method described above. The summation equation (2) makes clear that it is assumed that the reaction of one equivalent chlorite and one equivalent peroxodisulfate leads to an equivalent chlorine disulfate and also to an equivalent of a hydrogen sulfate radical, as described above. Accordingly, according to the present invention, the additional radical is preferably a hydrogen sulfate radical or a reaction product of the same, which was obtained by reaction with the hydrogen sulfate radical.

Because of the additional radical in the solution, said chlorine dioxide solution according to the invention comprises an additional strong oxidizing agent and therefore has an additional oxidizing effect, which suppresses or reduces the autocatalytic decomposition. Therefore, said chlorine dioxide solution according to the invention is advantageous compared to conventional chlorine dioxide solutions.

The present invention also relates to a kit, which in addition to the chlorine dioxide solution according to the invention comprises a separate suitable reduction agent, such as a separate sulfite-, disulfite-, thiosulfate-, sulfide- or nitrite solution. Preferably, the sulfite solution is a sodium sulfite solution. Alternately, solid sulfite can be used as well. The chlorine dioxide solutions in accordance with the invention can be destroyed in a short period of time in a simple and safe manner by adding sufficient quantities of sulfite. The addition of an aqueous sodium sulfite solution to the chlorine dioxide solution according to the invention instantly destroys the chlorine dioxide in the water- and air phase. The use of the kit according to the invention simplifies the transport, the handling as well as the destruction of the chlorine dioxide and allows a no-risk handling of the chlorine dioxide solution according to the invention. When in use, the destruction kit furthermore allows the application of solutions with higher chlorine dioxide concentrations with subsequent defined detoxification. The destruction of the chlorine dioxide has the additional advantage that only non-toxic chloride and, if sulfite is used, non-toxic sulfate is formed.

The present invention furthermore relates to the use of the aqueous chlorine dioxide solution described above as a disinfecting agent, as an oxidation- or bleaching agent and/or as deodorizing agent. The chlorine dioxide solutions according to the invention can be used, for example, for the disinfection of air, ground and water, such as drinking water, swimming pool water, wastewater, sanitary water, etc. in the medical field, in filters or in bio films. Furthermore, the chlorine dioxide solutions according to the invention can be used as oxidation- and/or bleaching agent, for example in various technical processes such as paper production, food production, etc. in the treatment of waste and sludge, or in cleaning agents. The chlorine dioxide solutions according to the invention can furthermore be used as deodorants, such as in odor treatment, for example in a wastewater canal, in industrial processes, in the home, etc. in solids, suspensions and cleaning agents. However, the applications listed above are not intended as a final list. Rather, the chlorine dioxide solutions according to the invention can be used in all suitable areas where their disinfecting, oxidizing and deodorizing effect is of use.

Furthermore, the chlorine dioxide solution according to the invention can be used to extract chlorine dioxide from said solution quantitatively into organic solvents by extraction with organic solvents such as ether, hydrocarbon, etc. This makes the chlorine dioxide accessible for other reactions that are limited to suitable organic solvents. This means that it can also be used in other fields where water is an impediment or counter-productive (for example because of corrosion due to air humidity, etc.).

The present invention furthermore relates to the use of an aqueous chlorine dioxide solution for the disinfection of drinking and swimming pool waters or for the processing of industrial- and waste waters, with the chlorine dioxide solution being obtained through a method that comprises the steps of providing chlorite, providing peroxodisulfate, and combining chlorite and peroxodisulfate in an aqueous system and in a molar ratio of peroxodisulfate to chlorite $[S_2O_8^{2-}]/[ClO_2^-]$ of greater than 1 with the formation of the aqueous chlorine dioxide solution.

The present invention furthermore relates to the use of an aqueous chlorine dioxide solution for the disinfection of drinking- and swimming pool waters; for the processing of process and waste waters or for the effective combating of bio films, with the solution comprising chlorine dioxide together with the hydrogen sulfate radical in the form of a radical pair associate.

In the following, especially preferred uses of the chlorine dioxide solutions according to the invention and/or chlorine dioxide solutions prepared with the method according to the invention are listed again. For example, the chlorine dioxide solutions according to the invention can be used in industrial processes.

Examples of technical processes comprise the non-destructive decontamination of membrane plants, for example RO plants, also in the medical field; the removal of moss on any type of materials; the removal of coatings, for example on motor vehicles, ships, aircraft; fighting odors in production processes; the industrial processing of waste water by decontaminating the waste water; physical-chemical separation of water, and recycling the residuals; corrosion protection in systems that carry wastewaters; the surface protection of paints, coatings of any type, plastics, wood, metal, ceramics, stone; microbial decontamination with long-term effect; the detoxification of surfaces and rooms (gaseous phase); keeping the air clean; cosmetic or medical applications, such as oral rinses, treatment of warts, removal of mites, specific destruction of cells, for external and internal application or for application against pathogenic bacteria; the oxidation of residual substances (medical drugs, X-ray contrast agents; oxidation products, cyanide, etc.); in wastewater (AOP) following clarification, oxidation of gaseous products ($H_2S$, NO, $NO_2$ as well as organic substances); as well as sterilization at low temperatures, such as surgical material. The chlorine dioxide solutions according to the invention can also be used for the oxidative heavy metal processing.

Furthermore, the chlorine dioxide solutions according to the invention can be used for the treatment of drinking water, for example in water plants for the permanent disinfection of drinking water, for removing the bio film in water pipes in the form of a standard disinfection or in form of a permanent disinfection. Furthermore, the chlorine dioxide solutions can be used for the emergency chlorination and/or disinfection of drinking water, for example after severe rainfall, after onset of decontamination (such as after a bacterial decontamination of a drinking water reservoir due to ground water, surface water or brackish water and for the removal of pathogens such as anthrax, cholera, etc.) or after natural disasters to provide drinking water disinfected in this manner and/or to maintain a supply of drinking water from poor quality surface water. Finally, the chlorine dioxide solutions can also be used in buildings (such as clinics, hospitals, assisted care facilities, administrative buildings, office buildings, residential buildings), swimming pools, motor vehicles (such as cars, trains, ships, aircraft) for the disinfection of warm- and cold water pipes, air conditioning systems, water treatment systems, boilers, wastewater systems, or the water in swimming pools and in this manner remove in particular Legionella and other bacteria and bio films and/or suppress the formation of bio films. Preferably, the chlorine dioxide solution according to the invention is used in form of a permanent disinfection for the removal of bio films, Legionella or other bacteria in drinking water pipes, air conditioning systems, water processing systems, boilers or swimming pools.

Other suitable applications in that field are substitutes for emergency disinfections, the disinfection of ground- or above ground tanks, the disinfection of valves and pipe lines, the disinfection after leaking pipes, the emergency disinfection after recontamination, the combating of bio films and bio film prophylaxis, the treatment of wastewater containing medical residue, as well as the removal of multi-resistant bacteria.

In air conditioning systems and cooling towers, the chlorine dioxide solutions according to the invention can be used for the removal of bio films from heat exchangers and pipe lines, for the removal of contamination, such as Legionella, for example; for continuing, permanent- or high-volume disinfection and for protection against corrosion.

In food production, the chlorine dioxide solutions according to the invention can be used for treatment of the process and rinsing water; for maintaining hygiene in the production process; for decontamination of transport vehicles; for animal-rearing; for the removal, combating and prophylaxis of infection sites, and for maintaining hygiene in the slaughtering area, for example during the processing, packaging or cleaning.

With fruit, produce and seeds, the chlorine dioxide solutions according to the invention can be used with a sustained effect for maintaining hygiene during the growth phase, during and after harvesting, for maintaining hygiene during processing, to extend shelf-life during packaging, to maintain the storage hygiene of seeds, to reduce the germination ability of seeds, for disinfection or for sterilization.

With trains, planes or ships, the chlorine dioxide solutions according to the invention can be used to maintain hygiene in the sanitary areas, air conditioning systems, to combat odors, for sustained ecological vegetation removal in the rail areas and of signs, etc.; for the disinfection of ships, for wastewater treatment, for the treatment of gray-, yellow- or black water, for the decontamination of the trim water and for the production of drinking water from sea water.

The chlorine dioxide solutions according to the invention are especially suitable for the removal of odors, for example in wastewater systems and in sewers. It furthermore serves as protection against corrosion in these systems because it puts a sustainable stop to the putrefaction. The removal of bio films with this solution is a very good surface protection for paints, coatings of any type, plastics, wood, metal, ceramics and stone. In doing so, the applied solution has a particularly sustained long-term effect. The long-term effect is the result of completely removing the bio film from the surface. Likewise, the solution can be used for the detoxification of surfaces and rooms (gaseous phase) and also for keeping the air clean. The chlorine dioxide solution can be used for the lasting cleaning, disinfection as well as sterilization of membranes. The stable radicals furthermore allow use in medical applications, such as oral rinses, wart treatments, mite removal, targeted cell destruction, and furthermore generally for external disinfection and for the destruction of pathogens.

The present invention furthermore relates to a device for the production of the chlorine dioxide solution described above. Said device for the production of the chlorine dioxide solution according to the invention is based on the idea that the method according to the invention for the production of a chlorine dioxide solution can not only be performed on a large-scale industrial basis, but is also suitable for use on a smaller scale. Therefore, an appropriate device for performing the method according to the invention can be present in single- or multi-family dwellings, for example, to continually provide the chlorine dioxide quantities required for the disinfection of drinking- and swimming pool waters.

Figure 1:
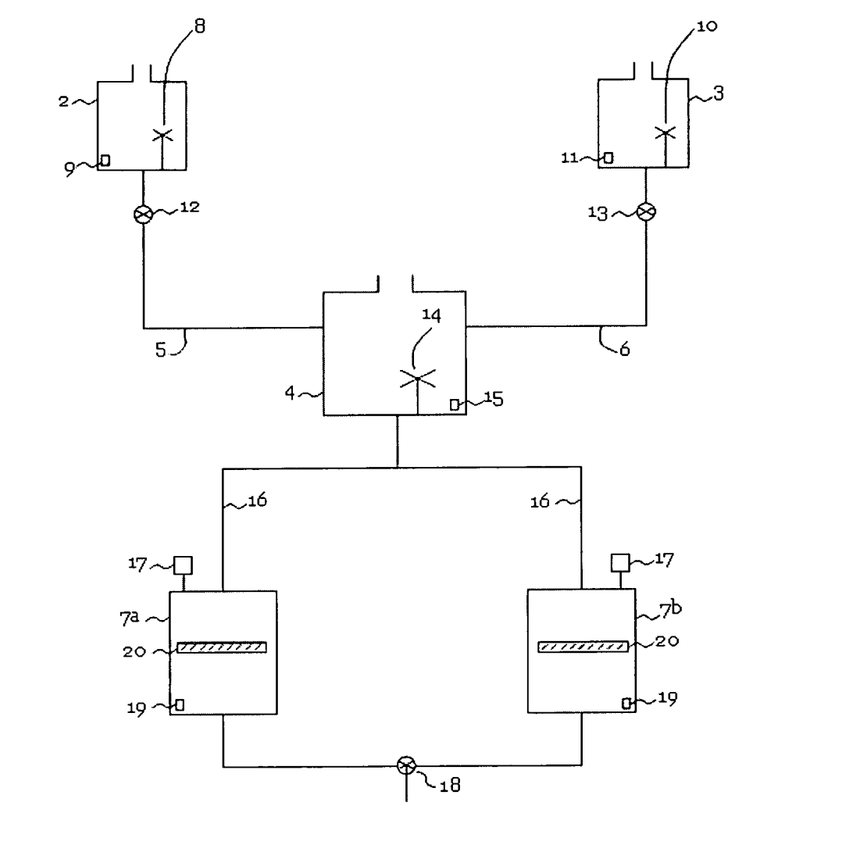
FIG. 1 shows a preferred embodiment of the device according to the invention for the production of a chlorine dioxide solution.

Given this background, the device according to the invention (1) for the preparation of the chlorine dioxide solution according to the invention comprises (a) at least one storage container for a chlorite component (2), (b) at least one storage container for a peroxodisulfate component (3), (c) at least one mixing container (4) that is connected, via a supply line for the chlorite component (5), to the at least one storage container for a chlorite component (2), or can be connected to the same, and which is connected, via a supply line for the peroxodisulfate component (6) with the at least one storage container for a peroxodisulfate component (3) or can be connected to the same;

(d) at least one storage container for the chlorine dioxide solution (7), which is connected to the mixing container (4) via at least one supply line for the chlorine dioxide solution (16) or can be connected to the same; and (e) a metering device (18) that is attached to the at least one storage container for the chlorine dioxide solution (7).

The device according to the invention is described below with reference to the accompanying drawing showing an example of a preferred embodiment because the tasks, features and advantages of the device according to the invention are easier to understand using the detailed description below and the accompanying drawing. Said description should be understood such that the embodiment shown in the drawing is also shown with merely preferred features that do not necessarily have to be present.

The device 1 comprises a storage container for a chlorite component 2. Said storage container 2 is designed to store the chlorite component in solid form and as aqueous solution, for example. In a preferred embodiment of the device according to the invention, the storage container 2 can comprise a mixing and/or stirring device 8 to generate in the storage container 2 an aqueous chlorite component by dissolving solid chlorite in water, with said dissolution being simplified with a mixing and/or stirring device 8. In another preferred embodiment, the storage container 2 contains one or more measuring cells 9, which are set up to determine the chlorite quantity and/or concentration in the storage container 2. For example, these can be measuring cells suitable for conductivity, pH-value, redox value, amperometric measuring cells or combinations thereof.

The device 1 furthermore comprises a storage container for a peroxodisulfate component 3. Said storage container 3 is designed to store the peroxodisulfate component in solid form and as aqueous solution, for example. In a preferred embodiment of the device according to the invention, the storage container 3 can comprise a mixing and/or stirring device 10 to generate in the storage container 3 an aqueous peroxodisulfate component by dissolving solid peroxodisulfate in water, with said dissolution being simplified with a mixing and/or stirring device 10. In another preferred embodiment, the storage container 3 contains one or more measuring cells 11, which are suitable for determining the peroxodisulfate quantity and/or concentration in the storage container 3. For example, this can be measuring cells suitable for conductivity, pH-value, redox value, amperometric measuring cells or combinations thereof.

The device 1 furthermore comprises a mixing container 4, which is connected or connectable to at least one storage container for a chlorite component 2 via a supply line for the chlorite component 5, and which is connected or connectable via a supply line for the peroxodisulfate component 6 to at least one storage container for a peroxodisulfate component 3. The supply lines 5 and 6 are set up to add the chlorite and/or peroxodisulfate components from the storage containers 2 and 3 to the mixing container 4. In a preferred embodiment, the supply lines 5 and 6 have metering devices 12 and 13, which are set up to control the quantity of the chlorite and/or peroxodisulfate to be supplied, and also to completely interrupt the supply of chlorite and/or peroxodisulfate. In an especially preferred embodiment, the supply lines 5 and 6 have metering devices 12 and 13, which are set up to control the quantity of chlorite and peroxodisulfate to be supplied in such a way that peroxodisulfate and chlorite are supplied to the mixing container 4 in ratio $[S_2O_8^{2-}]/[ClO_2^-]$ of greater than 1.

The mixing container 4 preferably comprises a mixing and/or stirring device 14, which is set up to mix the supplied chlorite- and peroxodisulfate component. Furthermore, the mixing container 4 preferably comprises one or more measuring cells 15, which are set up to determine the quantity and/or concentration of chlorine dioxide and/or chlorite and peroxodisulfate in the mixing container 4. With the appropriate measuring cells 15, it is possible to track the course of the reaction of chlorite and peroxodisulfate into chlorine dioxide. Furthermore, the mixing container 4 is preferably set up so water can be supplied to it. This is especially important if both components are supplied to the mixing container 4 as solids.

Furthermore, the device 1 according to the invention comprises one or a plurality of storage containers for the chlorine dioxide solution 7. In a preferred embodiment, the device 1 according to the invention comprises at least two storage containers for the chlorine dioxide solution 7a and 7b. The at least one storage container 7 is connected or connectable via at least one supply line 16 to the mixing container 4. The at least one storage container 7 is set up to store the chlorine dioxide solution produced with the method according to the invention until it is needed for the specific application. In a preferred embodiment of the device according to the invention, the at least one storage container 7 has a device for pressure control 17 which is set up to measure the pressure in the at least one storage container 7 and apply pressure to the at least one storage container 7. This is advantageous with respect to reducing the vapor pressure of the chlorine dioxide solution. In an especially preferred embodiment, the at least one storage container 7 also comprises a floating body 20 set up to cover the surface of the chlorine dioxide solution in the storage container 7. This is especially advantageous when the filling level of the storage container is low in view of reducing the vapor pressure of the chlorine dioxide solution.

Furthermore, the device 1 according to the invention comprises a metering device 18 that is attached to the at least one storage container for the chlorine dioxide solution 7. Said metering device 18 is set up to control the removal of the chlorine dioxide solution from the at least one storage container 7. The metering device 18 can be a metering pump, for example. If the device 1 comprises at least two storage containers 7a and 7b for the chlorine dioxide solution, it is advantageous if the metering device 18 is designed to remove chlorine dioxide solution either from storage container 7a or from storage container 7b. Furthermore, the storage container 7 preferably comprises one or more measuring cells 19 which are set up to determine the quantity and/or concentration of chlorine dioxide and/or chlorite and peroxodisulfate in the storage container 7. This makes it possible to determine the concentration of chlorine dioxide and its purity in the chlorine dioxide solution at any time.

The device in accordance with the invention makes it possible to produce chlorine dioxide solution in variable quantities and keep it available. The storage in at least two different storage containers 7a and 7b furthermore allows the continuous removal of finished chlorine dioxide solution. For example, the storage container 7b can be topped off while the solution is removed from storage container 7a, and vice versa.

In a preferred embodiment, the device according to the invention furthermore comprises a curing container, which is arranged between the mixing container 4 and the storage container 7. Said curing container is advantageously set up to accommodate and store the solutions combined in the mixing container 4 until the reaction of chlorite and peroxodisulfate into chlorine dioxide is complete. In an especially preferred embodiment, the curing container also comprises a device for pressure control.

Furthermore, the device according to the invention preferably comprises an automated process control unit, which, for example, is connected or is connectable to the measuring cells 9, 11, 15 and 19, the pressure control devices 17, as well as the metering devices 12 and 13. For example, said automated process control unit can control the quantity and the concentration of the chlorine dioxide solution to be produced by controlling the chlorite and peroxodisulfate quantities to be supplied.

In another preferred embodiment, the device 1 according to the invention is set up so that the chlorine dioxide solution is produced and stored in the dark. This can be done, for example, by designing the containers and supply lines in a light-impermeable fashion. However, it is also possible to arrange the device 1 in a light-impermeable box.

In another preferred embodiment, the device 1 according to the invention can be tempered. In doing so, it is especially preferred that the device 1 is set up so that in particular the mixing of the two starting products as well as the storage of the finished chlorine dioxide solutions can be done at temperatures in the range of about 0° C. to about 25° C. This can be done, for example, with suitable cooling means that cool the individual mixing and storage containers. However, it is also possible to arrange the entire device 1 in a type of refrigerator.

In another preferred embodiment of the invention, the device 1 according to the invention is set up to produce the chlorine dioxide solution continuously in continuous operation. In another preferred embodiment, the device 1 according to the invention is set up to produce the chlorine dioxide solution in batches in batch operation.

In a preferred development, the device according to the invention is set up for use as a small-scale system in a single- or multi-family dwelling. This is advantageous, for example, to provide the quantities of chlorine dioxide required for the disinfection of drinking- and swimming pool water continuously or in batch operation, as needed. In another preferred embodiment, the device according to the invention for the production of a chlorine dioxide solution is set up to be transported by accommodating it in a housing. Said housing can be any housing suitable for transport, such as a metal- or plastic housing, for example. Preferably, the transportable device is a device weighing less than 500 kg, especially preferably less than 100 kg. In this way, it is possible to transport the device according to the invention and therefore use the method according to the invention only after the chlorine dioxide solution has arrived at its place of use. For example, this can be in the form of small-scale systems in a single- or family dwelling.

In another preferred embodiment, the device according to the invention is set up for use as a large-scale system, such as a tank system, for example. This is advantageous, for example, to produce the chlorine dioxide solution according to the invention in large quantities and then fill it into smaller containers, if applicable, and sell and/or transport it. This has the advantage that the chlorine dioxide according to the invention does not have to be prepared onsite.

Finally, the present invention also relates to a radical pair associate comprising at least one chlorine dioxide radical as well as a hydrogen sulfate radical. Preferably, said radical pair associate furthermore has at least one water molecule and, if applicable, additional radical species. Said additional radical species can be suitable radical intermediate stages such as $OH^{\bullet}$, $SO4^{\bullet-}$ or $ClO^{\bullet}$, which formed proceeding from chlorine dioxide or the hydrogen sulfate radical. In a preferred embodiment, the radical pair associate according to the invention is stable, i.e. it is storage stable for at least 1 hour. In an especially preferred embodiment, it is stable for one day, even more preferred for one year. In an additional preferred embodiment, the radical pair associate according to the invention is not present in the presence of a buffer.

The invention is now explained in greater detail using examples.

EXAMPLES

Analytics:

The chlorine dioxide concentration in the chlorine dioxide solutions according to the invention can be determined using various measuring methods. In particular, the chlorine dioxide concentration can be determined with amperometry, photometry, iodometry, by titrating the chlorine dioxide solution with a sulfite solution, or with ion chromatography.

The analysis methods are described in detail in the work sheets of the German Association of Gas and Water Works (DVGW) W224 (February 2010), page 18ff with reference to DIN 38408-5.

In the examples below, photometry was used in particular to determine the chlorine dioxide concentration, as well as ion chromatography to determine the additional components such as chlorite, chlorate, perchlorate, hypochlorite and chlorine dioxide.

With photometry, the Lambert-Beer law applies without limitation. To determine the chlorine dioxide concentration with photometry, measurements are performed at a 360 nm wave length. The molar extinction coefficient is 1100+/−50 [1/mol*cm].

With ion chromatography, the components such as chlorite, chlorate, perchlorate, hypochlorite and chlorine dioxide are determined in combination. The conditions are known in the prior art and described, for example, in the dissertation of Petra Hübenecker, Bonn, 2010: "Studies on the creation of disinfection byproducts in the treatment of drinking water aboard navy units at sea using application conditions."

Example 1

Preparation of 60 Liters of an about 0.6% Aqueous Chlorine Dioxide Solution 56,530 g of purified water is weighed into a 60-liter canister. Separately, 1,970 g of a technical 24.5% sodium chlorite solution and 1,500 g sodium peroxodisulfate (99%) are weighed into separate containers. The peroxide and the chlorite are dissolved separately in a sufficient quantity of water from the canister. After the sodium chlorite solution has been placed into the container, the sodium peroxodisulfate solution is poured in and left to rest for 24 to 48 hours at 12° C. The chlorine dioxide yields are 88 to 98% relative to the sodium chlorite used.

Example 2

Production of 50 Snap Lid Bottles with 0.2 Liters Each of an about 0.6% Chlorine Dioxide Solution 9.65 liters of purified water are weighed into a 10-liter bucket. Separately, 100 g of a powdered 80% sodium chlorite (containing 20% sodium chloride) and 250 g sodium peroxodisulfate (99%) are weighed. Both solids are dissolved separately in a sufficient quantity of water from the bucket. The sodium chlorite solution is placed into the remaining water in the bucket and briefly mixed with the peroxide solution by stirring.

The finished mixture is filled into bottles and stored closed in the refrigerator for 2 to 3 days at 5 to 10° C. The chlorine dioxide yields are 85 to 99% relative to the sodium chlorite used.

Example 3

Preparation of One Liter of a 0.3% Chlorine Dioxide Solution 500 mg sodium chlorite (80%) are dissolved in 500 ml purified water and mixed with a solution of 2,500 mg sodium peroxodisulfate in 497 ml purified water. The bottle is closed and left standing in a refrigerator for 24 hours. The yield is >85% relative to the sodium chlorite used.

Example 4

Preparation of One Liter of a 0.6% Chlorine Dioxide Solution 10.00 g sodium chlorite (80%) are dissolved in 100 ml purified water. 105.00 g sodium peroxodisulfate (99%) are also dissolved in 100 ml purified water. Both solutions are added to 685 ml purified water. The bottle is closed and left standing in a refrigerator for 3 hours. The yield is >95% relative to the sodium chlorite used.

Example 5

Preparation of One Liter of a 0.6% Chlorine Dioxide Solution 10.00 g sodium chlorite (80%) are dissolved in 40 ml purified water. 330 g sodium peroxodisulfate (99%) are also dissolved in 620 ml purified water. The bottle is closed and left standing in a refrigerator for 30 minutes. The yield is >98% relative to the sodium chlorite used.

It was found that all chlorine dioxide solutions produced in the examples 1 to 5 are storage-stable, i.e. no decomposition worth mentioning (>5%) of the chlorine dioxide is noticed after one year. Furthermore, the solutions are even more stable if there are less by-products in the reaction mixture.

It was found that the finished product is membrane-permeable as radical pair associate and said radical pair associate has changed physical properties (vapor pressure, solubility, etc.).

The following values were determined for the vapor pressure of a 0.6% chlorine dioxide solution:

| Temperature [° C.] | Real gas concentration [g/ClO$_2$/m$^3$] | Calculated ClO$_2$- concentration [mbar] | Total pressure incl. water vapor [mbar] |
|---|---|---|---|
| 10 | 96 | 33 | 5 |
| 20 | 114 | 41 | 67 |
| 30 | 147 | 54 | 140 |
| 40 | 171 | 65 | 185 |
| 50 | 209 | 82 | 301 |

According to the literature (DVGW W224/1986, page 5), a warning that the solution has a tendency to explode is issued started at a ClO$_2$-concentration of 100 mbar (=10% vol, 300 g ClO$_2$/m$^3$).

On the other hand, it was found that the solutions according to the invention handle well and have no tendencies whatsoever for spontaneous decomposition and/or explosion. Even at high temperatures of 50° C., the product reacts only slowly with chlorate; at temperatures of 80 to 90° C. it reacts quickly. The solution is not flammable at any time. This has also been tested with chlorine dioxide concentrations of up to 4.5 wt %. If chloride dioxide solutions with concentrations of more than 2.5 wt % are produced, the pressure in the reaction container increases, which can be estimated according to the ideal gas law. At concentrations of more than about 4.5 wt %, the chlorine dioxide precipitates as an oily liquid.

If solutions with chlorine dioxide active substance concentrations of 0.01 to 4.5% are brought into contact with burning objects/open fire, said objects are extinguished even in 4.5% ClO$_2$ solutions; however, the gaseous phase decomposes in doing so. With solutions of <1% ClO$_2$, the reaction with the gaseous phase is not noticeable.

List Of Reference Symbols

1 Device for the production of the chlorine dioxide solution according to the invention
2 Storage container for a chlorite component
3 Storage container for a peroxodisulfate component
4 Mixing container
5 Supply line for the chlorite component
6 Supply line for the peroxodisulfate component
7, 7a, 7b Storage container for the chlorine dioxide solution
8 Mixing- and/or stirring device
9 Measuring cell in the storage container for a chlorite component
10 Mixing- and/or stirring device
11 Measuring cell in the storage container for a peroxodisulfate component
12 Metering devices for the chlorite component
13 Metering devices for the peroxodisulfate component
14 Mixing- and/or stirring device in the mixing container
15 Measuring cell in the mixing container
16 Supply line to the at least one storage container for the chlorine dioxide solution
17 Pressure control device
18 Metering device
19 Measuring cell
20 Floating body

The invention claimed is:

1. A method for producing an aqueous chlorine dioxide solution containing chlorine dioxide in a quantity of 0.3 to 4.5 wt %, comprising the steps:
   (a) providing chlorite,
   (b) providing peroxodisulfate, (c) combining chlorite and peroxodisulfate in an aqueous system and in a molar ratio of peroxodisulfate to chlorite $[S_2O_8^{2-}]/[ClO_2^-]$ of greater than 1 to form the aqueous chlorine dioxide solution;

wherein the aqueous chlorine dioxide solution is produced in the absence of a buffer; and wherein the aqueous chlorine dioxide solution contains chlorine dioxide in a quantity of 0.3 to 4.5 wt. % is storage stable and transportable, and does not contain a buffer other than any buffer produced by a reaction between the chlorite and the peroxodisulfate.

2. The method according to claim 1, wherein the molar ratio between peroxodisulfate and chlorite $[S_2O_8^{2-}]/[ClO_2^-]$ is greater than 2.

3. The method according to claim 1, wherein the molar ratio between peroxodisulfate and chlorite $[S_2O_8^{2-}]/[ClO_2^-]$ is between 1 and 2.

4. The method according to claim 1, wherein chlorite and peroxodisulfate are provided in the steps (a) and (b) as solids or in the form of an aqueous solution, and in step (c)

(c1) both components are dissolved in water before being combined if both components are provided as solids, or (c2) both components are introduced into an aqueous solvent in solid form at the same time or successively, or (c3) both solutions are combined when both componen s are provided in form of aqueous solutions, or (c4) both components are provided in an aqueous solution and introduced into an aqueous solvent at the same time or successively to produce the aqueous chlorine dioxide solution.

5. The method according to claim 4, wherein peroxodisulfate as well as chlorite are provided in form of aqueous solutions, with the peroxodi sulfate solution having a pH-value in the range of about 4 to about 6 and the chlorite solution having a pH-value in the range of about 10 to about 12.

6. The method according to claim 1, wherein the combining of the peroxodisulfate and chlorite is performed at a temperature in the range of about 0° C. to about 25° C.

7. The method according to claim 1, wherein the solution is stable for at least one year.

8. The method according to claim 7, wherein less than 5% of the chlorine dioxide decomposes over the one year.

9. The method according to claim 1, wherein the concentration of chlorine dioxide in the solution is in a range of about 0.3 wt % to about 1 wt %.

10. The method according to claim 9, wherein the concentration of chlorine dioxide in the solution is in a range of about 0.3 wt % to about 0.6 wt %.

11. The method according to claim 10, wherein the concentration of chlorine dioxide in the solution is in a range of about 0.5 wt % to about 0.6 wt %.

12. The method of claim 1, wherein said method does not involve producing an aqueous chlorine dioxide solution for onsite use.

* * * * *